United States Patent [19]
Filippini et al.

[11] Patent Number: 5,994,380
[45] Date of Patent: Nov. 30, 1999

[54] ANALOGS OF STROBILURINE HAVING FUNGICIDAL PROPERTIES, AND THEIR APPLICATION FOR CONTROLLING PHYTOPATHOGENOUS FUNGI

[75] Inventors: Lucio Filippini, San Donato Milanese; Isabella Venturini, Novara; Laura Colombo; Luigi Mirenna, both of Milan, all of Italy

[73] Assignee: Isagro Ricerca S.r.L., Milan, Italy

[21] Appl. No.: 09/174,451

[22] Filed: Oct. 19, 1998

[30] Foreign Application Priority Data

Oct. 17, 1997 [IT] Italy .................. MI97A2347

[51] Int. Cl.$^6$ .................. C07D 513/02; A01N 43/78
[52] U.S. Cl. .................. 514/368; 548/154
[58] Field of Search .................. 548/154; 514/368

[56] References Cited

FOREIGN PATENT DOCUMENTS

| | | |
|---|---|---|
| 0 370 629 | 5/1990 | European Pat. Off. . |
| WO 92/13830 | 8/1992 | WIPO . |
| WO 96/36615 | 11/1996 | WIPO . |

*Primary Examiner*—Robert Gerstl
*Attorney, Agent, or Firm*—Oblon, Spivak, McClelland, Maier & Neustadt, P.C.

[57] ABSTRACT

This invention refers to new analogs of strobilurine, having the general formula (I):

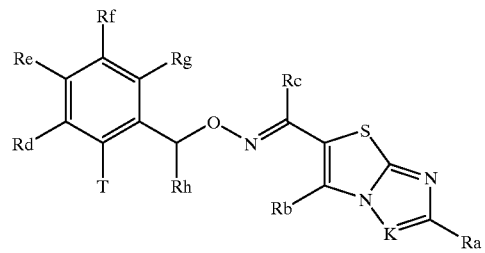

The compounds of formula (I) are endowed with good stability and high fungicidal activity against phytopathogenous fungi, combined with good selectivity for the vegetable it is designed to apply to.

40 Claims, No Drawings

ANALOGS OF STROBILURINE HAVING FUNGICIDAL PROPERTIES, AND THEIR APPLICATION FOR CONTROLLING PHYTOPATHOGENOUS FUNGI

This invention refers to new synthetic analogs of strobilurines, having fungicidal properties.

More in particular, this invention refers to new analogs of strobilurines having high fungicidal activity, a process for their preparation and their application in the agricultural sector for controlling pathogenous fungi.

The strobilurines are fungal metabolites chemically characterized by the presence of the 1-methoxycarbonyl-2-methoxyeten-1-yle group (PESTICIDE SCIENCE (1991), page 499). They act mainly as mitochondrial breathing inhibitors and have also evidenced good mycelial control of certain fungal species on in-vitro tests. However, the presence of dienic or trienic systems in the molecular skeleton renders these compounds unsuitable for practical applications, due to their excessive instability.

New analogs of strobilurines have now been found, which have a good stability and high fungicidal activity against phytopathogenous fungi combined with good selectivity for the vegetable they are designed to apply to.

The objects of this invention are therefore compounds having fungicidal activity, of the formula (I):

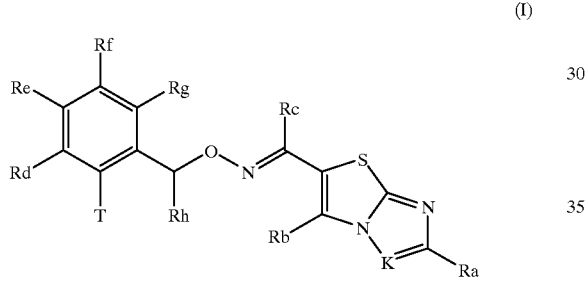

(I)

Where:

Ra, Rb, Rc, equal or different from each other, may be hydrogen; or a $C_1$–$C_6$-alkylic group, or a $C_1$–$C_6$-haloalkylic group; a $C_1$–$C_6$-alkoxylic or a $C_1$–$C_6$-haloalkoxylic group; a $C_1$–$C_6$-thioalkylic group, or a $C_1$–$C_6$-halothioalkylic group; a substituted N-aminic or bisubstituted N,N-aminic group with $C_1$–$C_6$-alkylic or $C_1$–$C_6$-haloalkylic groups; a $C_3$–$C_9$-cycloalkylic group; a non-aromatic heterocyclic compound composed of three to six atoms, containing at least one nitrogen atom and optionally an oxygen or sulfur atom; a $C_2$–$C_7$-carboalkoxylic group; a $C_2$–$C_7$-carbamoylic group; a phenylic or naphtylic group; a phenoxylic or napthoxylic group, a aromatic heterocyclic penta or hexa-atomic group containing from one to four hetero-atoms optionally chosen among nitrogen, oxygen and sulfur; a aromatic heterocyclic penta or hexa-atomic benzo-condensed group containing from one to four hetero-atoms optionally chosen between nitrogen, oxygen and sulfur; said $C_1$–$C_6$-alkylic, $C_1$–$C_6$-alkoxylic, $C_1$–$C_6$-thioalkylic groups and said $C_3$–$C_9$-cycloalkylic and hetero-cyclic non-aromatic groups containing at least one nitrogen atom and said phenylic, naphtylic, phenoxylic, naphtoxylic and penta or hexa-atomic aromatic hetero-cyclic, aromatic hetero-cyclic penta or hexa-atomic benzo-condensate, aromatic hetero-cycloxylic penta or hexa-atomic, aromatic hetero-cycloxylic penta or hexa-atomic benzo-condensate groups even if optionally substituted by one or more groups of an equal or different nature, optionally chosen between a halogen such as fluorine, chlorine, or bromine, a $C_1$–$C_6$-alkylic, a $C_1$–$C_6$-haloalkylic group; a $C_1$–$C_6$-alkoxylic, a $C_1$–$C_6$-haloalkoxylic group; a phenylic, a cyano-group; a $C_2$–$C_7$-carboalkoxylic group; a nitro-group;

K represents a nitrogenous group: =N—; or a =C(Ri)— group;

Rd, Re, Rf, Rg, Rh and Ri are equal or different from each other and may be hydrogen; or a $C_1$–$C_6$-alkylic or a $C_1$–$C_6$-haloalkylic group; a $C_1$–$C_6$-alkoxylic or a $C_1$–$C_6$-haloalkoxylic group; a $C_1$–$C_6$-thioalkylic or a $C_1$–$C_6$-halothioalkylic group; a $C_3$–$C_9$-cycloalkylic group; a $C_2$–$C_7$-carboalkoxylic group; a $C_2$–$C_7$-carbamoylic group; a phenylic, a cyano-group; a halogen group; Rd combined with Re, or Re with Rf, or Rf with Rg may even represent the alkendienylic chain —HC=CH—C=CH—;

T represents one of the following groups:

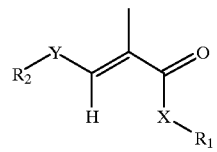

IIa

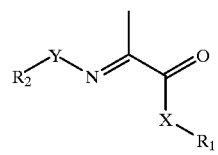

IIb

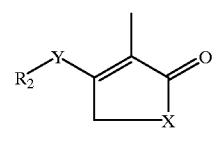

IIc

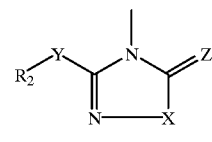

IId

Where:

X, Y, equal or different from each other, may be oxygen, sulfur, or a nitrogenous group (III):

—N (R3)—     (III)

or may represent a direct bond;

R1 may be hydrogen; a $C_1$–$C_6$-alkylic or a $C_1$–$C_6$-aloalkylic group: or if X assumes the significance of nitrogenous group (III), it may also be a $C_1$–$C_6$-halkoxylic or a $C_1$–$C_6$-haloalkoxylic group;

R2 may be hydrogen; a $C_1$–$C_6$-alkylic or a $C_1$–$C_6$-haloalkylic group;

R3 may represent hydrogen; or a $C_1$–$C_6$-alkylic or a $C_1$–$C_6$-haloalkylic group;

Z may be oxygen or sulfur.

The compounds of formula (I) may exhibit an isomeric geometric structure. One type of isomeric structure refers to the double oxymic bond as explicitly shown in formula (I). Another type of isomeric structure refers to the double bond present in the group indicated as T, when T represents a structure of the formula (IIa) or (IIb). The aim of this invention covers the preparation and application of compounds of formula (I), isomerically pure or as mixtures of isomers in any proportion.

The preferred configuration is at any rate that of the group labeled T, when T represents a structure of the formula (IIa) or (IIb), wherein the group R2—Y—turns out to be E (trans) with respect to the group —CO—X—R1.

A $C_1$–$C_6$-alkylic means a linear or branched $C_1$–$C_6$-alkylic group. Examples of such a group are: methyl, ethyl, propyl, isopropyl, butyl, isobutyl, and tertiary butyl.

A $C_1$–$C_6$-aloalkylic group means a linear or branched alkylic group, substituted with one or more halogen atoms equal or different from each other, optionally chosen between fluorine, chlorine, bromine or iodine. Examples of such a group are: fluoromethyl difluoromethyl, trifluoromethyl, trichloromethyl, 2,2,2-trifluoromethyl, 2,2, 2-trichloromethyl, 2,2,3,3-tetrafluoropropyl, 2,2,3,3,3-pentafluoropropyl, trichloromethyl, 2,2,2,-trichloroethyl, 1,1-dichloro-2,2,2-trifluoroethyl and dibromomethyl.

A $C_1$–$C_6$-alkoxylic group means a $C_1$–$C_6$-alkoxylic group, in which the aliphatic portion is represented by a $C_1$–$C_6$-alkylic group, as previously defined. Examples of such a group are: methoxyl, ethoxyl, and isoproxyl.

A $C_1$–$C_6$-halkoxylic group means a $C_1$–$C_6$-aloalkoxylic group, where the aliphatic portion is a $C_1$–$C_6$-haloalkylic group as previously defined. Examples of such a group are: trifluoromethoxyl, 1,1,2,2-tetrafluoroethoxyl, 3,3,3,2,1, 1-penta-fluoro-propyloxyl.

A $C_1$–$C_6$-thioalkylic group stands to mean a $C_1$–$C_6$-thioalkylic group, where the aliphatic portion is a $C_1$–$C_6$-alkylic group, as previously defined. Examples of such a group are: thiomethyl, thioethyl, and thioisopropyl.

A $C_1$–$C_6$-halothioalkylic group stands to mean a $C_1$–$C_6$-halothioalkylic group where the haloalkylic portion is a $C_1$–$C_6$-haloalkylic group, as previously defined. Examples of such a group are: difluorothiomethoxyl, trifluorothiormethoxyl, and 1,1,2,2-tatrafluorothioethoxyl.

Examples of an N-substituted or N.N-disubstituted aminic group with $C_1$–$C_6$-alkylic or $C_1$–$C_6$-haloalkylic groups are: N-methylamine, N,N-dimethylamine, N-methyl-N-ethylamine, and N-methyl-N-isopropylamine.

Examples of an aromatic hetero-cyclic group composed of three up to six atoms and containing at least one nitrogen and optionally one oxygen or sulfur atom are: 4-morpholyl, 1-azetidynil, and 1-piperidazinyl.

A $C_3$–$C_9$-cycloalkylic group stands to mean a cycloalkylic group whose ring is constituted by 3–6 carbon atoms. Examples of a $C_3$–$C_9$-cycloalkylic group are: cyclopropyl, 1-methylcyclopropyl, cyclobutyl, cyclopentyl, and cyclohexyl.

A $C_2$–$C_7$-carboalkoxylic group stands to mean a carboalkoxylic group group where the aliphatic portion is a $C_1$–$C_6$-alkylic group, as previously defined.

Examples of a $C_2$–$C_7$-carboalkoxylic group are: carbomethoxyl, carboethoxyl, and carboisopropoxyl.

A $C_2$–$C_7$-carbamoylic group stands to mean a carbamoylic group which may be N-mono or N,N-disubstituted with $C_1$–$C_6$-alkylic groups as previously defined. Examples of a $C_2$–$C_7$-carbamoylic group are: carbamoyl (H2N—CO—), N-methylcarbamoyl (H(CH3)N—CO—), and N,N-dimethyl-carbamoyl ((CH3) 2N—CO—).

Examples of a penta or hexa-atomic aromatic heterocyclic group containing one to four hetero-atoms optionally chosen between nitrogen, oxygen and sulfur are: pyrrole, imidazole, pyrazole, triazole, isooxazole, oxazole, thiazole, isothiazole, furane, thiophene, pyridine, pyrazine and pyrimidene.

Examples of a penta or hexa-atomic aromatic heterocyclic group containing one to four hetero-atoms optionally chosen between nitrogen oxygen and sulfur benzo-condensate are: indole, benzofurane, benzothiophene, benzothiazole, benzooxazole, and benzoisooxazole.

Examples of a penta or hexa-atomic aromatic heterocyclicoxylic group containing one to four hetero-atoms optionally chosen between nitrogen, oxygen and sulfur are: pyridiloxyl and pyrimidoxyl.

Examples of a penta or hexa-atomic aromatic heterocycloxylic benzo-condensed group containing one to four hetero-atoms optionally chosen between nitrogen, oxygen and sulfur are: benzooxazolyloxyl, and benzothilazolyloxyl.

The compounds having the formula (I) may be obtained in numerous synthetic ways.

For example, they can be obtained by the process described in the Scheme A:

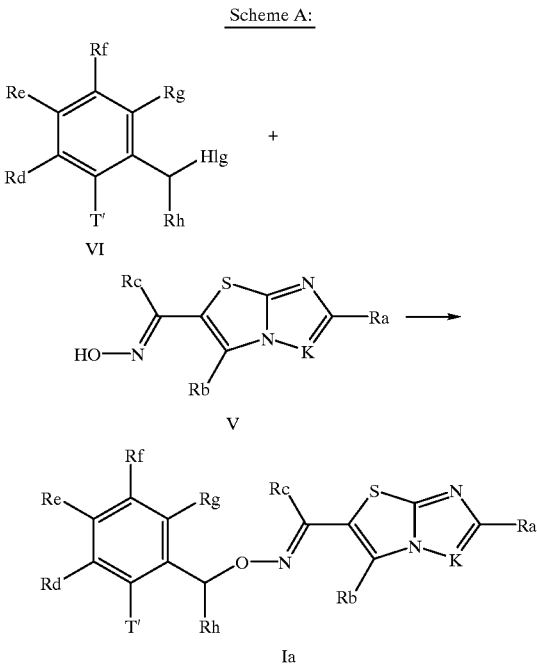

An intermediate of formula IV, in which the Hlg group may represent a halogen such as chlorine, bromine or iodine, or may also assume the significance of a sulfonic acid ester such as for instance the matansulfonic, paratoluenesulfonic or trifluoromethansulfonic acid, is reacted with an oxyme of the formula V, in the presence or absence of an inorganic base, such as for instance sodium or potassium carbonate, in an aprotic dipolar organic solvent such as for instance: N,N-dimethylformamide, N-methylpyrrolidone and dimethylsulfoxide or in an aromatic solvent such as: toluene, xylene, or in a polar solvent, as per example: acetonitrile, acetone or ethyl-acetate, at a temperature between 0° C. and the boiling point of the solvent chosen. This achieves a compound of the formula (Ia), where T' may be the same group T as previously defined, or a precursor group of T, such as for instance a bromide, iodine, nitro or carboxylic group —COO—R1, where R1 may be hydrogen or a $C_1$–$C_6$-alkylic group.

In the case in which T' represents a bromine or iodine atom, it is possible to obtain a T-group of the formula (IIa), or a T-group of the formula (IIc) by reacting the corresponding halide (Ia) according to the processes described for examples in SYNLETT (1995), page 32; or in TETRAHEDRON Vol 47 (1991), page 8285, or in the Italian patent application no. MI96A001837.

If T' is a carboxylic COOR1 group as previously defined, it will be possible to convert said T' group to a formula T-group by one of the methods described in EP 564984.

If T' is on the other hand a nitro group, said T' group may be converted to a T-group to obtain a compound of the formula (I), by following the process described in Scheme B.

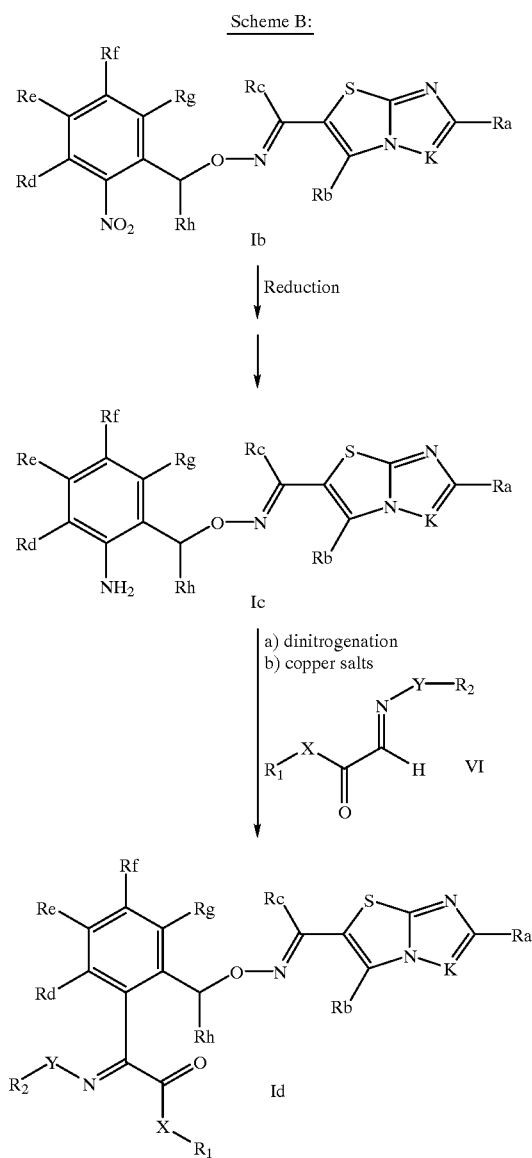

The nitroderivative (Ib) is reduced to the corresponding aminic derivative (Ic) by one of the processes known in the literature, for instance those reported in MARCH, ADVANCED ORGANIC CHEMISTRY, Second Edition, pages 1125–1126, International Student Edition, or in R. C. LAROCK, Comprehensive Organic Transformations (1989), pages 412–415, VCH Publishers Inc.

The aminic compound Ic is subsequently reacted as a diazonium salt with an appropriate compound of the formula (VI), according to the experimental conditions outlined for example in the JOURNAL OF CHEMICAL SOCIETY (1954), page 1297, or the JOURNAL OF CHEMICAL SOCIETY (1955), page 3094, and then alkylated with an appropriate alkylating agent of the formula (VII):

$$R^2 \; Hlg' \qquad (VII)$$

Where Hlg may assume the meanings already described for the Hlg group of Scheme A, in addition to the meaning of an alkylsulfate —O—SO$_2$—O—R2, preferably in the presence of an inorganic basis such as sodium or potassium carbonate, at a temperature in the range from –30° C. to the boiling point of the solvent chosen, thus to obtaining a compound (Id) of the general formula (I), in which T is a group IIb.

The aminic Ic group may further be converted to a compound of the formula (I) where T represents a group IId by one of the processes described for example in W09636615, in W09636616 or in W097199335.

The compounds of formula IV, in which the group T' represents the group T as previously defined, are easily obtained by known processes.

One possibility is in the following process described in Scheme C:

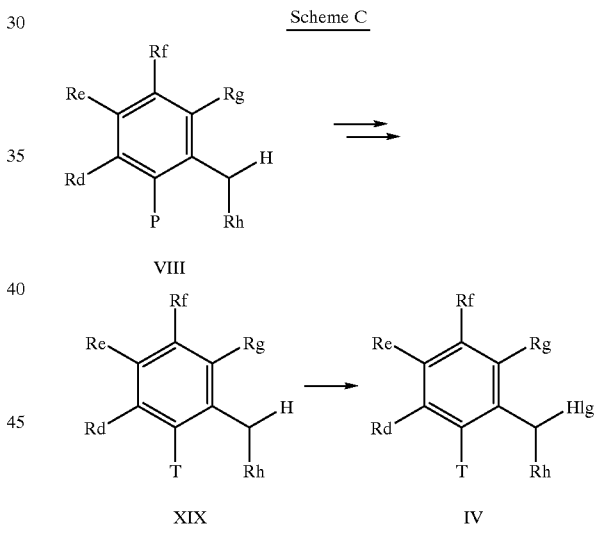

This scheme utilizes as a synthetic precursor a compound of formula VIII, where P may be a halogen chosen between chlorine, bromine and iodine, or a nitro group or a carboxylic —COO—R1 group, as previously defined. If P is a bromine or chlorine atom or a nitro group or a carboxylic COO—R1 group, the T-group of the compound (XIX) may be obtained by converting P in a manner similar to that previously described for obtaining the T group from the T' group.

If P is a halogen, it is still possible to obtain a T group by forming an organometallic reagent, such as for instance a Grignard reagent, which is subsequently reacted with oxalyl-chloride and then with an appropriate compound R1—X—H, where R1 and X assume the meanings previously defined, while operating for example as described in EP535928; or the organometallic reagent is reacted with an appropriate derivative of oxalic acid, as described in BER- ICHTE Vol. 81 (1948), page 314, or in the JOURNAL OF ORGANIC CHEMISTRY, Vol. 46 (1981), page 211, or in SYNTHETIC COMMUNICATION Vol. 11 (1981), page 943. The oxalate thus obtained (a compound of formula VIII, in which P represents an oxalyl group of the formula (X);

—CO—CO—X—R1    (X)

is finally converted to a compound of formula (XIX) in which T represents a group of formula IIa, by condensation with an appropriate ilide, such as for instance an ilide of formula (XI):

Ph3P=CH—Y—R2    (XI)

while conducting the reaction in an ethereal solvent such as ethyl-ether, tetrahydrofurane or dioxane or in an aproptic dipolar solvent, such as dimethylsulfoxide, as for instance described in TETRAHEDRON LETTERS, Vol. 28 (1987), page 475; or this oxalate may be converted to a compound of formula (XIX) in which T represents a group of formula IIb, by reacting it with an appropriate O-alkylhydroxylamine of formula (XTT):

R2—O—NH2    (XII)

in an alcoholic solvent, such as anhydrous or aqueous methanol, ethanol, or isopropanol, in the presence or absence of a base such as sodium acetate, sodium bicarbonate or sodium carbonate, at a temperature in a range from 20° C. to the boiling point of the solvent chosen, or by reacting it with hydroxylamine hydrochloride, under conditions similar to the foregoing, and subsequently with an appropriate alkylating agent of formula (VII):

R—Hlg'    (VII)

as previously defined, in the presence of an inorganic base, such as sodium or potassium carbonate, at a temperature in the range of –30° C. to the boiling temperature of the solvent chosen.

If P is an aminic group, a T group of the formula (IId) can be obtained by utilizing one of the processes described in WO9636615, in WO9636616 or in WO 9719935.

The compounds of formula (XIX) thus obtained are converted into a compound (IV), for instance by treating them with an appropriate halogenating agent such as for instance N-bromosuccinimide, in a solvent such as carbontetrachloride, chloroform, tetrachloroethane, or acetic acid, in the presence or absence of catalytic quantities of a radical chain priming agent such as benzoylperoxide or AIBN or of a light source, at a temperature in the range from the ambient temperature T to the boiling point temperature of the solvent chosen.

Any compound of formula (I) or of formula (XIX), or of formula (IV) where the radical T represents a group of formula (IIa) or any group of formula (IIb) in which the symbol X represents oxygen may be converted to a corresponding group T of formula (IIa) or (IIb) in which the symbol X represents a nitrogenous group (III), by reacting it with the appropriate amine (XIII):

H—N (R3)—R2    (XIII)

in a polar solvent such as dimethylsulfoxide, N,N-dinethylformamide, N-methylpyrrolidone or acetonitrile, in the presence or absence of water, at a temperature ranging from –25° C. to the boiling point of the solvent in question.

The compounds of formula (V), where K is the group =N—, can for example be obtained by the process illustrated in Scheme D:

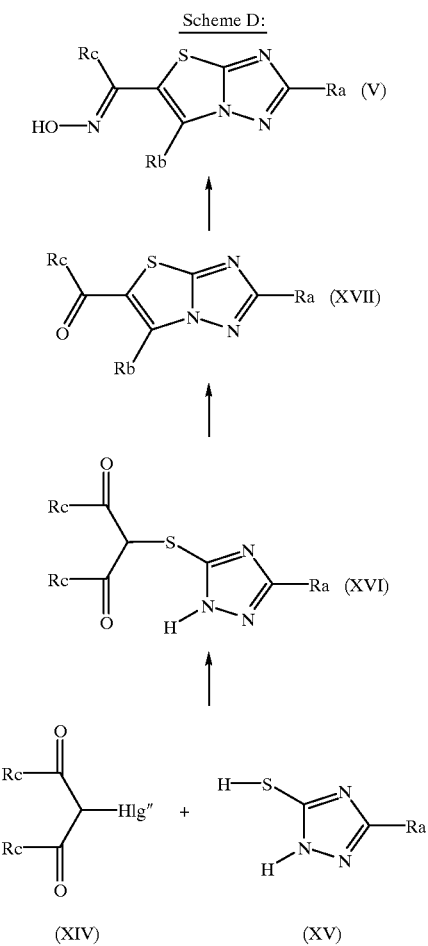

The halide (XIV) in which the symbol Hlg" assumes the meaning of chlorine, bromine, and iodine or of a metasulfonic acid ester, as symbolized by Hlg, is reacted with a thiotriazole of formula (XV). The reaction is carried out in ethereal solvents such as tetrahydrofurane or dioxane, in the presence of water and of a base, such as sodium bicarbonate, carbonate or acetate, or the reaction is carried out using an an alcoholic solvent, even in the absence of a base, at a temperature in the range from –10 C. to the boiling point of the solvent chosen. The adduct of formula (XVI) is then cyclized to obtain the ketone (XVII) in an alcoholic ambient, in the presence of an acid such as hydrochloric acid, which may be that formed in-situ during the foregoing reaction between the compounds (XIV) and (XV), and in the presence or absence of a dehydrating agent, such as trimethylorthoformiate or the triethylorthoformiate, or the cyclization can be achieved in the presence of thionyl chloride, which acts simultaneously as an acidity donor and dehydrating agent. The ketone (VII) is then reacted with hydroxylamine chlorohydrate, both in the presence or absence of a base such as ethyl acetate or an alkaline bicarbonate or carbonate, in an alcoholic solvent such as methanol, ethanol or isopropanol, so as to obtain the desired compound of formula (V). The compounds of formula (V), where K represents the group —C(Ri)— can be obtained for instance by the process outlined in Scheme E:

Scheme E

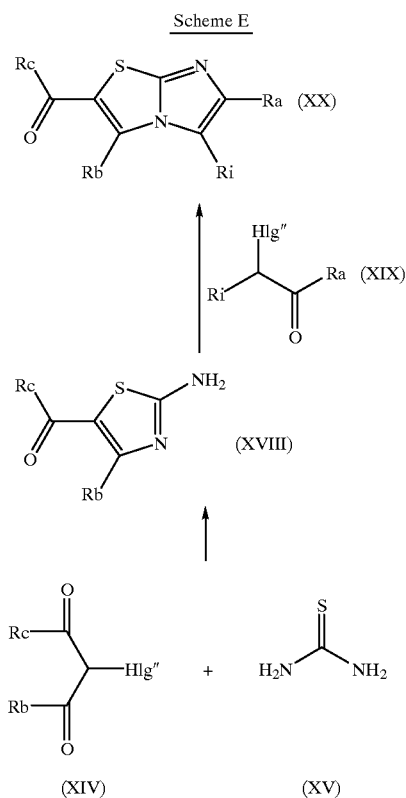

The halide of formula (XIV) is made to react with thiourea in an alcoholic solvent such as ethanol, or in water or in a mixture of water and other solvent such as tetrahydrofurane or dioxane, at a temperature in the range from 25° C. to the boiling point of the solvent system chosen, in the absence or presence of a base such as an alkaline carbonate or bicarbonate, thus obtaining a 2-aminothiazole of the formula (XVIII), which is subsequently reacted with an appropriate aloketone of formula (XIX) in an ethereal solvent at ambient temperature, then in an alcoholic solvent at the boiling point, or directly in an alcoholic solvent at a temperature which may vary from an ambient level to the boiling point of the solvent chosen. This produces a ketone of formula (XX), which is converted to the corresponding oxyme of formula (V) in a manner similar to that formerly described for the ketone of formula (VII).

The halides of formula (XIV) are commercial products or may be easily obtained by any processes described in the technical literature, for instance by using halogenating agents such as bromine, chlorine, N-bromosuccinimide, and sulforyl chloride.

The compounds having the general formula (I) are endowed with a particularly high fungicidal activity against phytopathogenic fungi attacking the cultures of grape, sugar beets, cereals, Cucurbitacee and fruit trees.

The plant diseases which may be treated with the compounds of the general formula (I) as an object of this invention arc for example the following:

*Helminthosporium teres* on cereals;
*Erysiphe graminis* on cereals;
*Puccinia spp.* on cereals;
*Plasmopara viticola* on vine;
*Phytium* on vegetables;
*Phytophtor spp.* on vegetables;
*Septoria spp.* on cereals;
*Spaerotheca fuliginea* on the *Cucurbitacee* (for ex. cucumber)
*Rhynchosporium* on cereals;
*Podospaera leucotricha* on the apple tree;
*Uncinula necator* on vine;
*Venturia spp.* on fruit trees;
*Pyricularia oryzae* on rice;
*Botrytis cinerea;*
*Fusarium spp.* on cereals; etc.

The compounds having the general formula (I) are capable of exerting a fungicidal action of both a curative and preventative nature, and moreover exibit a weak or zero phytotoxicity.

For practical agricultural uses it is often useful to have some fungicidal compositions containing one or more compounds of the general formula (I), The application of these compositions may occur on any portion of the plant, for example on the leaves, stems, branches or roots, or on the seeds themselves prior to seeding, or on the soil harboring the plant.

Various compositions may be used, including dry powders, wettable powders, emulsifiable concentrates microemulsions, pastes, granulated materials, solutions, suspensions, etc.: the composition chosen depends on the specific application.

The compositions are prepared in a known manner, for instance by diluting and dissolving the active ingredient in a solvent and/or a solid diluent, in the eventual presence of surfactants. The following may be used as solid solvents or supports: silica, kaoline, bentonite, talcum, fossil flour, dolomite, calcium carbonate, magnesia, gypsum, clays, synthetic silicates, attapulgite and sepiolite.

As liquid solvents, apart from water water of course, a number of solvents may be used, such as for instance aromatics (xylenes or mixtures of alkylbenzenes), chlorinated aromatics (chlorobenzene), paraffins (petroleum fractions), alcohols (methanol, propanol, butanol, octanol, glycerine), amines, amides (N,N-dimethylformamide, N-methylpyrrolidone), ketones (cyclohexanone, acetone, acetophenone, isoforone, ethylamylketone), and esters (isobutylacetate).

As surfactants it is possible to use sodium, calcium and triethanolamine salts or triethylamine salts of alkylsulfonates, alkylarylsulfonates, polyethoxylated alkylphenols, fatty alcohols condensed with ethylene oxide, polyoxyethylated fatty acids, polyoxyethylated sorbitol esters or lignosulphonates.

The compositions may also contain special additives for particular purposes, such as for instance tackifying agents such as gum arabic, polyvinylalcohol, and polyvinylpyrrolidone.

If desired, the compositions object of this invention can also be admixed with other compatible active ingredients, such as for instance fungicides, growth regulators, antibiotics, herbicides, insecticides, and fertilizers.

Some example of fungicides which may be included in the composition of this invention are alanicarb, ampropylfos, anilazine, azaconazole, azoxystrobin, BAS 490 F, BAY KTU 3616, benalaxyl, benomyl, biloxazol, binapacryl, bitertanol, blasticidine S, bromoconazole, bupirimate, butenaclor, butiobate captafol, captan, carbondazim, carboss, chlorobenzothiazone chinoethionate, chloroneb, chlorotalonil, clozolinate, clozylacon, copper salts, cyclohexylimide, cymoonaxyl, cyproconazole, cyprofurane, cyprodinil, CGA 245 704, diclofuanid, diclone diclobutrazole, diclomezine, dichloran, didecyl- or dimethyl-ammonium chloride, dictofencarb, difeconazole, dimefluazole, dimetconazole, dimetomorf, dimetirimol, diniconazole, dinocap, dipiritione, ditalimfos, ditianon, dodemorf, dodine, doguadine, edifenfos, epoxyconazole, otaconazole, etirimol, etossiquin, etridiazole, famoxadone, fenaminosulf, fenapanil, fenarimol, fenbuconazole, fenturan, fenpiclonil, fenpropidin, fenpropimorf, fentin acetate, ferbam, ferimzone, fluazinam, fludioxonil, fluorimide, fluotrimazole, flutolanil, flutriafol, fluzilasol, folpet, fuberidazole, furalaxyl, cis-urconazole, quazatine, ICI A S504, hydroxy-isooxazole, imesazole imazalil, imibenconazole, ipconazole, iprobenfos, iprodione, isoprotiolane, kasagumicine, kresoximethyl, mancozeb, maneb, menapyrim, mepronil, metalaxyl, metconazole, metfuroxam, metiram, metsulfovax, myclobutanil, neoasozin, nuarimol, ofurace, oxadixyl, oxicarboxyn, perfurazoate, penconazole, pencycuron, fenazine oxide, fosetil-A1, phosphoric acids, phtalide, polioxyn D, polyram, probenazole, prochloraz, procimidone, propamocarb, propiconazole, propineb, proprionic acid, protiocarb, pyracarbolid, pyrazofos, pyrimethanil, pyrifenox, pyroquilon, pyroxifur, pyrrolnitrin, quaternary ammonium compounds, quinconazole, quinomethionate, quintozene, rabenazol, sodium pentachlorophenate, SSF 126, SSF 129, spiroxamine, streptomycine, sulfur, tebuconazole, tecloftalam, tecnazene, thiabendazole, ticarbanyl, ticyofen, thifluzamide, 2-(thiocyanomethylthio) benzothiazole, methyithiofanate, tiram, timibenconazole, methyl-ticlofos, tolylfluanid, triacetate salt of 1,1' imino-di-(octamethylcene) diguanidine, triadimefon, triadimenol, triazabutyle, triazaoxide, tricyclazole, tridemorf, triforine, triflumizol, triticonazole, validamycine A, vapam, vinclozolin, zineb and ziram.

The concentration of active ingredient in the subject compositions may vary within a broad range, depending on the active ingredient, the culture, the pathogen, the environmental conditions and the type of formulation adopted. The concentration of active ingredient generally ranges from 0.1% to 95%, preferably from 0.5% to 90%.

The examples outlined below are given for illustrative and non-limiting purposes for this invention The elementary composition of each compound prepared in the following examples is reported in the Tables 1 and 2.

EXAMPLE 1
Preparation of the Compound 2.3

A solution of 3.1 g of (2-bromethylphenyl) methyl-methoxyiminoacetate in 15 cm$^3$ of N,N-dimethylformamide is admixed with 1.6 g of potassium carbonate. After 20' a solution of 2.4 g oxyme of 6-acetylthiazole-[3,2-b][1,2,4]-triazole in 10 cm$^3$ of N,N-dimethylformamide is slowly dripped in at 25° C. After 24 hours at ambient temperature the reacted substance is diluted with water and extracted with ethyl acetate. The organic phase is dried on sodium sulphate and concentrated at reduced pressure. The raw product is then purified by chromatography on a silica gel, while using a mixture of hexane and ethyl acetate in a 1:1 v/v ratio as an eluent. This produces 2.1 g of the desired product. [NMR: ppm, 200 MHz: 2.05 (3H, s); 2.30 (3H, s); 2.40 (3H, s); 3.65 (3H, s); 3.85 (3H, s); 4.90 (2H, s); 7.20 (4H, m)].

EXAMPLE 2
Preparation of the Compound 2.4

A solution of 2.0 g of the compound (2.3) in 6 cm$^3$ of N,N-dimethylformamide is admixed with 6 cm$^3$ of an aqueous solution of 30% N-methylamine. After 3 hours of vigorous agitation the reaction product is diluted with water and extracted with ethyl acetate. The organic phase is dried on sodium sulphate and evaporated at reduced pressure. The raw product is crystallized with a mixture of hexane and ethyl acetate in a 2:8 v/v ratio to obtain 1.1 g of compound (2.4). [NMR: ppm, 200 MHz: 2.18 (3H, s); 2.49 (3H, s); 2.57 (3H, s); 2.85 (3H, d); 3.92 (3H, s) 5.08 (2H, s); 6.79 (1H, m); 7.12 (1H, m); 7.37 (3H, m)].

EXAMPLE 3
Preparation of the Compounds 1.1–5, 2.1, 2.2 and 2.5–18.

In a manner similar to that described in Example 1 and Example 2, the compounds 1.1–5, 2.1, 2.2 and 2.5–18 were prepared, whose elementary composition is reported in the Tables 1 and 2 attached below.

EXAMPLE 4

Determination of the preventive fungicidal activity against peronospora of the vine (*Plasmopara viticola*). Some leaves of a Dolcetto vine culture, grown in jars in a controlled environment (20±1° C., 70% of relative humidity) are treated by irrigating both sides of the leaves with the compounds 1.1–1.5 and 2.1–2.18 in a hydroacetonic solution containing 20% acetone by volume.

After 24 hours of exposure to the controlled environment, the plants are irrigated on both sides of the leaves with an aqueous suspension of conides of *Plasmopora viticola* (200,000 conides per cm$^3$). The plants are kept in a moisture-saturated environment at 21° C. for the incubating time of the fungus. At the end of this period (7 days), the fungicidal activity is rated according to a percentage scale ranging from 100 (healthy plant) to 0 (totally infected plant). All the synthesized compounds have demonstrated a control of over 90%, at a concentration of 2,000 ppm.

EXAMPLE 5

Determination of the preventive fungicidal activity against cucumber oidium (*Sphaeroteca fuliginea*).

Some leaves of a cultivar Marketer cucumber, grown in jars in a controlled environment (20±1° C., 70% of relative humidity) are treated by irrigating both sides of the leaves with the compounds no. 1.1, 1.2, 1.3, 2.1, 2.2 and 2.3 in a hydroacetonic solution containing 20% acetone by volume.

After 24 hours of exposure to the controlled environment, the plants are irrigated on both sides of tile leaves with an aqueous suspension of conides of *Sphaeroteca fuliginea* (200,000 conides per cm$^3$).

The plants are maintained in a moisture saturated environment at 21° C., for the incubation period of the fungi.

At the end of this period (8 days), the fungicidal activity is rated according to a percentage scale ranging from 100 (healthy plant) to 0 (totally infected plant).

All the synthesized compounds have demonstrated a control of over 90%, at a concentration of 500 ppm.

Table 1: Examples of compounds of the general formula (I), where K represents a group =N—, T is the group IIa, the groups $R_1$, $R_2$, Rb and Rc represent the methyl group, and the Rg and Rh groups are hydrogen.

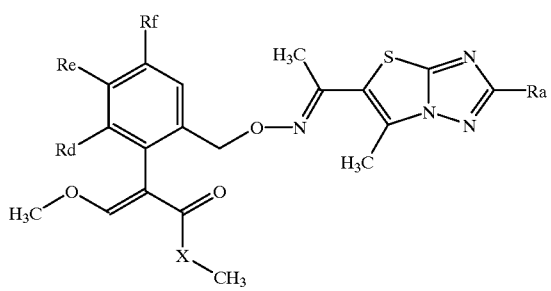

| No. | Ra | Rd | Re | Rf | X | C | H | N |
|---|---|---|---|---|---|---|---|---|
| 1.1 | H | H | H | H | O | 56.68 (56.70) | 5.50 (5.51) | 13.90 (13.92) |
| 1.2 | methyl | H | H | H | O | 57.70 (57.68) | 5.80 (5.81) | 13.47 (13.45) |
| 1.3 | phenyl | H | H | H | O | 62.73 (62.74) | 5.49 (5.48) | 11.69 (11.71) |
| 1.4 | 4-chlorophenyl | H | H | H | O | 58.52 (58.53) | 4.91 (4.91) | 10.90 (10.92) |
| 1.5 | 4-methoxyphenyl | H | H | H | O | 61.42 (61.40) | 5.57 (5.55) | 11.03 (11.02) |

Table 2: Examples of compounds of the general formula (I), where K represents a group =N—, T is the group IIb, the groups $R_2$, Rb and Rc represent the methyl group, and the Rg and Rh groups are hydrogen.

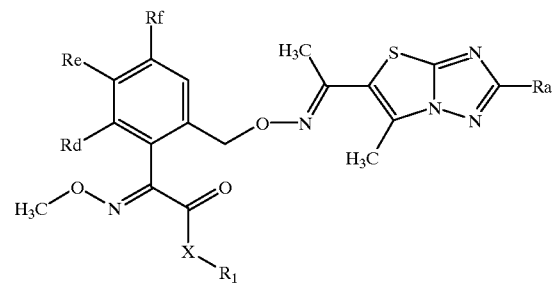

| No. | Ra | Rd | Re | Rf | X | $R_1$ | C | H | N |
|---|---|---|---|---|---|---|---|---|---|
| 2.1 | H | H | H | H | O | $CH_3$ | 53.60 (53.59) | 5.25 (5.25) | 17.33 (17.36) |
| 2.2 | H | H | H | H | NH | $CH_3$ | 53.71 (53.72) | 5.53 (5.51) | 20.87 (20.88) |
| 2.3 | methyl | H | H | H | O | $CH_3$ | 54.66 (54.66) | 5.52 (5.55) | 16.75 (16.77) |
| 2.4 | methyl | H | H | H | NH | $CH_3$ | 54.80 (54.79) | 5.79 (5.81) | 20.16 (20.18) |
| 2.5 | methyl | H | H | H | NH | H | 53.75 (53.72) | 5.50 (5.51) | 20.88 (20.88) |
| 2.6 | methyl | $CH_3$ | H | H | NH | $CH_3$ | 55.78 (55.80) | 6.07 (6.09) | 19.51 (19.52) |
| 2.7 | methyl | H | H | $OCH_3$ | NH | $CH_3$ | 53.80 (53.80) | 5.83 (5.87) | 18.82 (18.02) |
| 2.8 | methyl | H | H | F | NH | $CH_3$ | 52.54 (52.52) | 5.33 (5.34) | 19.30 (19.34) |
| 2.9 | methyl | HC=CH—HC=CH | | H | NH | $CH_3$ | 59.22 (59.21) | 5.60 (5.62) | 18.00 (18.01) |
| 2.10 | n-hexyl | H | H | H | NH | $CH_3$ | 59.25 (59.24) | 7.05 (7.04) | 17.28 (17.27) |
| 2.11 | isopropyl | H | H | H | NH | $CH_3$ | 56.75 (56.74) | 6.35 (6.35) | 18.92 (18.90) |
| 2.12 | cyclohexyl | H | H | H | NH | $CH_3$ | 60.21 (60.22) | 6.89 (6.87) | 16.85 (16.85) |
| 2.13 | 4 chlorophenyl | H | H | H | NH | $CH_3$ | 56.22 (56.19) | 4.90 (4.91) | 16.36 (16.38) |
| 2.14 | 4-chlorophenyl | H | $CH_3$ | H | NH | $CH_3$ | 56.99 (56.97) | 5.18 (5.16) | 15.93 (15.95) |
| 2.15 | 2-methoxyphenyl | H | H | H | NH | $CH_3$ | 59.02 (59.04) | 5.51 (5.55) | 16.52 (16.52) |
| 2.16 | 4 methoxyphenyl | H | H | H | NH | $CH_3$ | 59.03 (59.04) | 5.54 (5.55) | 16.55 (16.52) |
| 2.17 | 4 methoxyphenyl | H | $CH_3$ | H | NH | $CH_3$ | 56.75 (56.75) | 5.80 (5.79) | 16.11 (16.08) |
| 2.18 | methoxymethyl | H | H | H | NH | $CH_3$ | 54.68 (54.66) | 5.51 (5.55) | 16.77 (16.77) |

We claim:

1. A compound of the formula (I):

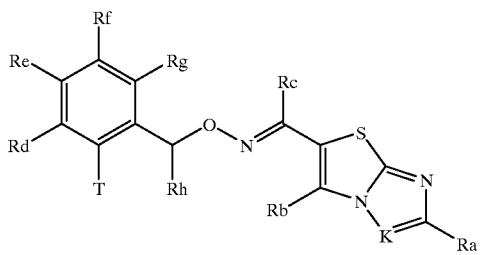

wherein:

Ra, Rb, Rc, which are the same or different, are hydrogen; $C_1-C_6$-alkyl; $C_1-C_6$-haloalkyl; $C_1-C_6$-alkoxy; $C_1-C_6$-haloalkoxy; $C_1-C_6$-alkylthio; $C_1-C_6$-haloalkylthio; N-substituted or N,N-disubstituted amine with $C_1-C_6$-alkyl, $C_1-C_6$-haloalkyl, or $C_3-C_9$-cycloalkyl group; a non-aromatic heterocyclic group containing from three to six atoms, containing at least one nitrogen atom and optionally an oxygen or sulfur atom; $C_2-C_7$-alkoxy carbonyl; $C_2-C_7$-carbamoyl; phenyl; naphthyl; phenoxy; naphthoxy, an aromatic heterocyclic penta- or hexa-atomic group optionally containing from one to four hetero-atoms selected from the group consisting of nitrogen, oxygen and sulfur; an aromatic heterocyclic penta- or hexa-atomic benzo-condensed group optionally containing from the group consisting of nitrogen, oxygen and sulfur; said $C_1-C_6$-alkyl; $C_1-C_6$-alkoxy; $C_1-C_6$-alkylthio and $C_3-C_9$-cycloalkyl and heterocyclic non-aromatic groups containing at least one nitrogen atom; and said phenyl, naphthyl, phenoxy, naphthoxy, penta- or hexa-atomic aromatic heterocyclic, aromatic heterocyclic penta or hexa-atomic benzo-condensed, penta- or hexa-atomic aromatic hetero-cycloxy, aromatic hetero-cycloxy penta or hexa-atomic benzo-condensed, optionally substituted by one or more groups, which are the same or different from each other, and which are halogen; $C_1-C_6$-alkyl; $C_1-C_6$-aloalkyl; $C_1-C_6$-alkoxy; $C_1-C_6$-haloalkoxy; phenyl; cyano $C_2-C_7$-alkoxycarbonyl or nitro; K is =N— or =C(Ri)—;

wherein;

Rd, Re, Rf, Rg, Rh and Ri, which are the same or different from each other, are hydrogen; $C_1-C_6$-alkyl, $C_1-C_6$-haloalkyl; $C_1-C_6$-alkoxy; $C_1-C_6$-haloalkoxy; $C_1-C_6$-alkylthio; $C_1-C_6$-haloalkylthio; $C_3-C_9$-cycloalkyl; $C_2-C_7$-alkoxycarbonyl; a $C_3-C_7$-carbamoyl; phenyl; cyano; halogen; or Rd combined with Re; or Re combined with Rf; or Rf combined with Rg is —HC=CH—CH=CH—;

T is one of the following groups:

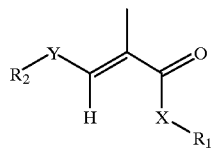 IIa

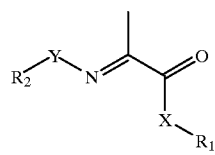 IIb

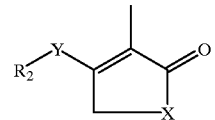 IIc

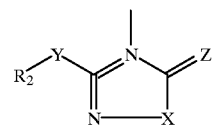 IId wherein:

X, Y, are the same or different from each other, and are oxygen, sulfur, or a nitrogenous group of the formula (III);

—N(R3)—    (III)

or are each a direct bond;
wherein:

R1 is hydrogen; $C_1-C_6$-alkyl; $C_1-C_6$-haloalkyl; or where X is the group (III), R1 is also $C_1-C_6$-alkoxy or $C_1-C_6$-haloalkoxy;

R2 is hydrogen; $C_1-C_6$-alkyl or $C_1-C_6$-haloalkyl;

R3 is hydrogen; or $C_1-C_6$-alkyl or $C_1-C_6$-haloalkyl; and

Z is oxygen or sulfur.

2. The compound of claim 1, where Ra, Rb, Rc which are the same or different are each:

hydrogen; or $C_1-C_6$-alkyl group; $C_1-C_6$-alkoxy; $C_3-C_9$-cycloalkyl; phenyl; or phenyl substituted by one or more groups, which are the same or different, and are halogen or $C_1-C_6$-alkoxy.

3. The compound of claim 1, where Rd, Re, Rf, Rg, Rh and Ri, which are the same or different from each other, are hydrogen; or $C_1-C_6$-alkyl, or $C_1-C_6$-haloalkyl; $C_1-C_6$-alkoxy, halogen or Rd jointly with Re, or Re jointly with Rf, or Rf jointly with Rg, is an alkendienylic chain, —HC=CH—CH=CH—.

4. The compound of claim 1, in which the group T has a structure of the formula (IIa) or (IIb), in which:

X, Y, are the same or different from each other, and are oxygen or the nitrogenous group of the formula (III):

—N(R3)—    (III)

wherein:

R1 is hydrogen or $C_1-C_6$-alkyl;

R2 is hydrogen or $C_1-C_6$-alkyl; and

R3 is hydrogen.

5. The compound of claim 1, which is isomerically pure or a mixture of isomers.

6. The compound of claim 1, where the group T has a structure of the formula (IIa) or IIb), where the group R2-Y is in the form E (trans) relative to the group —CO—X—R1.

7. The compound of claim 1, which is methyl(E)-2-[2-[[(((5-methylthiazole[3,2-b][1,2,4]-triazol-6-yl)ethylidene)amino)oxy]methyl]phenyl]-3-methoxypropenoate.

8. The compound of claim 1, which is methyl(E)-2-[2-[[(((3,5-dimethylthiazole[3,2-b][1,2,4]-triazol-6-yl)ethylidene)amino)oxy]methyl]phenyl]-3-methoxypropenoate.

9. The compound of claim 1, which is methyl(E)-2-[2-[[(((3-phenyl-5-methylthiazole[3,2-b][1,2,4]-triazol-6-yl)ethylidene)amino)oxy]methyl]phenyl]-3-methoxypropenoate.

10. The compound of claim 1, which is methyl(E)-2-[2-[[(((3-(4-chlorophenyl)-5-methylthiazole[3,2-b][1,2,4]-triazol-6-yl)ethylidene)amino)oxy]methyl]phenyl]-3-methoxypropenoate.

11. The compound of claim 1, which is methyl(E)-2-[2-[[(((3-(4-methoxyphenyl)-5-methylthiazole[3,2-b][1,2,4]-triazol-6-yl)ethylidene)amino)oxy]methyl]phenyl]-3-methoxypropenoate.

12. The compound of claim 1, which is methyl(E)-2-methoxyimino-2-[2-[[(((5-methylthiazole[3,2-n][1,2,4]-triazol-6-yl)ethylidene)amino)oxy]methyl]phenyl]acetate.

13. The compound of claim 1, which is N-methyl(E)-2-methoxyimino-2-[2-[[(((5-methylthiazole[3,2-b][1,2,4]-triazol-6-yl)ethylideno)amino)oxy]methyl]phenyl]acetamide.

14. The compound of claim 1, which is methyl(E)-2-methoxyimino-2-[2-[[(((3,5-dimethylthiazole[3,2-b][1,2,4]-triazol-6-yl)ethylidene)amino)oxy]methyl]phenyl]acetate.

15. The compound of claim 1, which is N-methyl(E)-2-methoxyimino-2-[2-[[(((3,5-dimethylthiazole[3,2-b][1,2,4]-triazol-6-yl)ethylidene)amino)oxy]methyl]phenyl]acetamide.

16. The compound of claim 1, which is (E)-2-methoxyimino-2-[2-[[(((3,5-dimethylthiazole[3,2-b][1,2,4]-triazol-6-yl)ethylidene)amino)oxy]methyl]phenyl]acetamide.

17. The compound of claim 1, which is N-methyl(E)-2-methoxyimino-2-[2-[[(((3,5-dimethylthiazole[3,2-b][1,2,4]-triazol-6-yl)ethylidene)amino)oxy]methyl]-6-methylphenyl]acetamide.

18. The compound of claim 1, which is N-methyl(E)-2-methoxyimino-2-[2-[[(((3,5-dimethylthiazole[3,2-b][1,2,4]-triazol-6-yl)ethylidene)amino)oxy]methyl]-4-methoxyphenyl]acetamide.

19. The compound of claim 1, which is N-methyl(E)-2-methoxyimino-2-[2-[[(((3,5-dimethylthiazole[3,2-b][1,2,4]-triazol-6-yl)ethylidene)amino)oxy]methyl]4-fluorophenyl]acetamide.

20. The compound of claim 1, which is N-methyl(E)-2-methoxyimino-2-[2-[[(((3,5-dimethylthiazole[3,2-b][1,2,4]-triazol-6-yl)ethylidene)amino)oxy]methyl]naphtyl]acetamide.

21. The compound of claim 1, which is N-methyl(E)-2-methoxyimino-2-[2-[[(((3-hexyl-5-dimethylthiazole[3,2-b][1,2,4]-triazol-6-yl)ethylidene)amino)oxy]methyl]phenyl]acetamide.

22. The compound of claim 1, which is N-methyl(E)-2-methoxyimino-2-[2-[[(((3-(2propyl)-5-dimethylthiazole[3,2-b][1,2,4]-triazol-6-yl) ethylidene)amino)oxy]methyl]phenyl]acetamide.

23. The compound of claim 1, which is N-methyl(E)-2-methoxyimino-2-[2-[[(((3-cyclohexyl-5-dimethylthiazole[3,2-b][1,2,4]-triazol-6-yl)ethylidene)amino)oxy]methyl]phenyl]acetamid.

24. The compound of claim 1, which is N-methyl(E)-2-methoxyimino-2-[2-[[(((3-(4-chlorophenyl)-5-dimethylthiazole[3,2-b][1,2,4]-triazol-6-yl)ethylidene)amino)oxy]methyl]phenyl]acetamide.

25. The compound of claim 1, which is N-methyl(E)-2-methoxyimino-2-[2-[[(((3-(4-chlorophenyl)-5-dimethylthiazole[3,2-b][1,2,4]-triazol-6-yl) ethylidene)amino)oxy]methyl]-6-methylphenyl]acetamide.

26. The compound of claim 1, which is N-methyl (E)-2-methoxyimino-2-[2-[[(((3-(2-methoxyphenyl)-5-dimethylthiazole[3,2-b][1,2,4]-triazol-6-yl) ethylidene)amino)oxy]methyl]phenyl]acetamide.

27. The compound of claim 1, which is N-methyl (E)-2-methoxyimino-2-[2-[[(((3-(4-methoxyphenyl)-5-dimethylthiazole[3,2-b][1,2,4]-triazol-6-yl) ethylidene)amino)oxy]methyl]phenyl]acetamide.

28. The compound of claim 1, which is N-methyl (E)-2-methoxyimino-2-[2-[[(((3-(4-methoxyphenyl)-5-dimethylthiazole[3,2-b][1,2,4]-triazol-6-yl) ethylidene)amino)oxy]methyl]-6-methylphenyl]acetamide.

29. The compounds of claim 1, which is N-methyl(E)-2-methyoxyimino-2-[2-[[(((3-methoxymethyl-5-dimethylthiazole[3,2-b][1,2,4]-triazol-6-yl)ethylidene)amino)oxy]methyl]phenyl]acetamide.

30. A process for preparing the compound of claim 1, having the formula (I), which comprises reacting a compound of the formula (IV) with a compound of the formula (V):

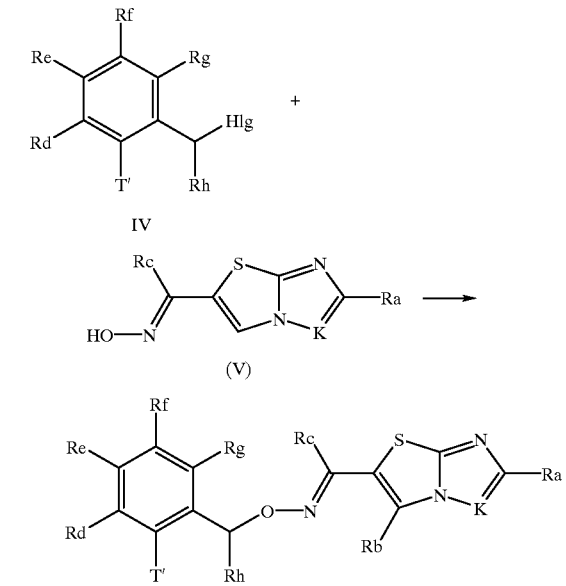

in a solvent at a temperature of between 0° C. and a boiling temperature of the solvent, optionally in the presence of an inorganic base wherein said solvent is an aprotic dipolar solvent, an aromatic solvent or a polar solvent.

31. The process of claim 30, wherein the group Hlg of the intermediate of formula IV is halogen or an ester of sulfonic acid.

32. The process of claim 30, wherein the inorganic base is sodium carbonate or potassium carbonate.

33. The process of claim 30, wherein the:
aprotic dipolar organic solvent is used which is selected from the group consisting of N,N-dimethylformamide, N-methylpyrrolidone, and dimethylsulfoxide.

34. The process of claim 33, wherein the aromatic solvent is used which is selected from the group consisting of toluene and xylene.

35. The process of claim 33, wherein the polar solvent is selected from the group consisting of acetonitrile, acetone and ethyl acetate.

36. The process of claim 30, wherein T' is as defined for T, or is precursor of T.

37. The process of claim 30, wherein T' is bromine or iodine, or nitro or a —CO—R1 carboxylic group, wherein R1 is hydrogen or $C_1$–$C_6$-alkyl.

38. A fungicidal composition, comprising an effective amount of one or more of the compounds of claim 1, alone or in admixture with solid supports, liquid diluents, surfactants, or other additives or active ingredients.

39. A method for combatting fungus infections, which comprises applying an effective amount of one or more of the compounds of claim 1, to plants, leaves, stems, branches, roots or in seeds prior to sowing or on soil where said plants are grown.

40. The method for combatting fungus infections of claim 39, wherein said one or more compounds are in the form a composition containing solid supports, liquid diluents, surfactants, or other additives or active ingredients.

* * * * *